United States Patent
Raia et al.

(10) Patent No.: US 7,086,528 B2
(45) Date of Patent: Aug. 8, 2006

(54) DEVICE FOR STORING AND DISPENSING SUBSTANCES AND METHOD OF MAKING AND USING SAME

(75) Inventors: Gioacchino Raia, Seefeld (DE); Reinhold Nowak, Adelshofen (DE); Marc Peuker, Schondorf (DE)

(73) Assignee: 3M ESPE AG, Seefeld (DE)

( * ) Notice: Subject to any disclaimer, the term of this patent is extended or adjusted under 35 U.S.C. 154(b) by 111 days.

(21) Appl. No.: 10/220,611

(22) PCT Filed: Feb. 28, 2001

(86) PCT No.: PCT/EP01/02243

§ 371 (c)(1),
(2), (4) Date: Dec. 16, 2002

(87) PCT Pub. No.: WO01/64547

PCT Pub. Date: Sep. 7, 2001

(65) Prior Publication Data

US 2003/0146117 A1    Aug. 7, 2003

(30) Foreign Application Priority Data

Mar. 1, 2000    (DE) ............................... 100 09 623

(51) Int. Cl.
*B65D 69/00*    (2006.01)
(52) U.S. Cl. ...................... 206/229; 206/63.5; 206/209

(58) Field of Classification Search ............... 206/15.2, 206/15.3, 63.5, 229, 230, 361, 438, 570
See application file for complete search history.

(56) References Cited

U.S. PATENT DOCUMENTS

| | | | | |
|---|---|---|---|---|
| 3,713,779 A | * | 1/1973 | Sirago et al. ............... | 206/219 |
| 5,054,610 A | * | 10/1991 | Ajello ........................ | 206/229 |
| 5,240,415 A | | 8/1993 | Haynie | |
| 5,616,336 A | | 4/1997 | Ayad | |
| 5,660,273 A | * | 8/1997 | Discko, Jr. .................. | 206/229 |
| 6,105,761 A | * | 8/2000 | Peuker et al. ............... | 206/229 |

FOREIGN PATENT DOCUMENTS

| | | |
|---|---|---|
| DE | 3122237 | 1/1983 |
| DE | 37 02 157 | 6/1988 |
| EP | 0 895 943 | 2/1999 |

* cited by examiner

*Primary Examiner*—Luan K. Bui
(74) *Attorney, Agent, or Firm*—Crowell & Moring LLP (57) ABSTRACT

A device for storing and applying material, especially dental material, comprises a first zone comprising a first and a second film that define at least one first chamber that receives a first substance, and a pouch separated from the chamber for withdrawing the first substance. The separation between the pouch and the first chamber is provided with a through opening that can be selectively opened. The device further comprises a second zone with a second chamber that is not linked with the first section by way of a through opening that can be selectively opened.

17 Claims, 4 Drawing Sheets

DEVICE FOR STORING AND DISPENSING SUBSTANCES AND METHOD OF MAKING AND USING SAME

BACKGROUND AND SUMMARY OF THE INVENTION

The invention relates to a device for storing and dispensing dental material in particular, comprising a first portion having a first foil and a second foil which form at least a first chamber for receiving a first substance, and a pouch which is separate from the chamber and is used for removing the first substance. The area between the first chamber and the pouch has a passage area that can be selectively opened. The device further comprises a second portion with a further chamber which is not connected either to the first chamber or to the pouch of the first portion via a passage area that can be selectively opened.

In the dental field in particular, it is often necessary to perform a large number of manual operations in succession.

To fill a cavity of a tooth, for example, with a plastic filling, first a primer usually has to be applied or blown onto the hard dental substance, followed by a bonding agent, then exposed to light, if appropriate, before the actual filling can be applied.

While the adhesive substances of primer and bonding agent are usually in liquid form packaged in bottles, the filling material is present as a highly viscous material in screw-cap tubes or is pressed out from what are known as compules.

The dentist applying a filling thus first has to take the primer and bonding agent in the form of a liquid from one package and then remove the filling material in the form of a highly viscous compound from a different package.

The time spent in doing this is not inconsiderable. In addition, the primer and bonding agent from one manufacturer are often not adapted to the chemical composition of the filling material from another manufacturer, which can result in reduced adhesion values on the tooth. Nor can operating errors be ruled out when opening, dispensing and using the substances in sequence from the different packages.

Small quantities of liquid can be stored and applied, for example, using receptacles in the form of blister packs. For example, two recesses separated from one another are provided in the thermoformed part of the package closed off by a removable foil. The first recess can contain a small amount of liquid, and a brush can be placed in the other recess.

WO-96/03326, for example, describes a disposable receptacle which has cavities for storing a medicament and an applicator. Both cavities are protected from contamination by means of a peelable cover foil. In one embodiment, by pressing on the cavity containing the medicament, the medicament is transferred into the cavity containing the applicator in order to wet the applicator.

Moreover, a device is described which has two cavities for storage of medicaments and which is suitable for administering a medicament consisting of two components. The cavities can be opened separately and closed again. The two cavities are opened and closed in the same way.

U.S. Pat. No. 3,835,834 discloses a treatment kit which has two cavities in a main body, cavities containing a care substance on the one hand and a swab on the other. The main body containing the care substance and the swab is protected from contamination by means of a sealing foil.

EP 0 895 943 A discloses a device for storing and dispensing a free-flowing substance, with a container made up of two foils which are connected to one another to form a chamber for receiving the substance and a pouch which is separate from the chamber and used for removing the substance, the separation between the chamber and the pouch having a passage area that can be selectively opened.

A disadvantage of the known devices is that the devices often contain only a pretreatment agent after whose application a further substance, for example, a filling material, usually has to be applied to the pretreated site. It can happen that the pretreatment agent is not fully adapted to the nature of the further substance. This can lead to unsatisfactory results. The known devices are not suitable for storing and dispensing substances having different rheological properties.

The object of the present invention can primarily be regarded as that of making available a device which avoids the aforementioned problems.

A further object can be regarded as that of making available a device with which it is possible to store different substance classes inside one package and to dispense them in order.

A further object can be regarded as that of making available a device with which it is possible to store, in one package, low-viscosity to liquid substances, on the one hand, and highly viscous to kneadable substances, on the other.

This object is achieved by a device and by a method for using the device, as described in the claims.

The words "comprise" or "include" within the meaning of the invention precede a nonexhaustive list of features. The word "one" is to be interpreted as an indefinite quantity with the meaning of "at least one".

The invention has the following advantages:

The presence of a second portion with a further chamber which cannot be connected to the first portion, which has at least one first chamber, via a passage area that can be selectively opened permits the storage of at least one further substance which is normally used in sequence after application of the first substance.

The second portion of the device can be connected to the first portion in any way, the aim being to ensure that when the substance is dispensed from the first chamber of the first portion, it cannot pass into the chamber of the second portion. Consequently, the chambers of the first portion cannot be connected to the chamber or chambers of the second portion via an openable passage area. For easier handling of the device, the second portion is preferably designed so that it can be detached from the first portion. A design of the connection piece which permits detachment by manual tearing is particularly expedient. This can be obtained, for example, by perforating the connection piece. However, any other design of the connection piece between the two portions is also conceivable and possible, for example, by adhesive bonding with a further foil.

Since the substance located in the further chamber of the second portion is usually adapted to the nature of the substance in the other chamber of the first portion, this reduces the risk of using substances which are not compatible with the first substance.

It is further ensured that all of the substances stored in the device are filled on the same date, so that incompatibilities of the substances due to different expiry times can be excluded.

Thus, the device is on the whole easy to handle since the first substance, which is located in the first chamber, can first be transferred into the pouch for removal, without complications and awkward opening of the device. After application of the substance from the pouch, a second substance is stored in the same device and made ready for application. The second substance, which usually differs in consistency from the first substance, is stored in a chamber which can be opened in a different way than the first chamber.

Whereas the substance located in the first chamber can be dispensed by exerting pressure on the device, without removing a cover layer, a cover sheet usually has to be torn off manually to remove the second substance.

The device is thus distinguished by the fact that it has two portions with at least one chamber, each for receiving in each case one substance, which substances are for their part to be removed from the device in different ways, and the individual chambers are opened in different ways.

If appropriate, the chambers of the first portion contain at least a further receptacle, preferably in the form of a cushion, which can be opened by exerting pressure.

The presence of a separate receptacle for receiving a substance ensures that in the storage state the substance does not come directly into contact either with the passage area that can be selectively opened or with the foils forming the chamber.

In this way, damage to the device, in particular the foils forming the device, is made difficult. This permits a longer storage life of the device containing the substance.

In this connection, it has proven advantageous to produce the receptacle using materials which greatly impair or prevent the diffusion of volatile substances.

Depending on the material for the receptacle, aggressive substances can in this way also be stored and handled without problems, and without having to forego the advantageous properties of the foils normally used to form the container.

The term aggressive substances includes both corrosive substances (for example acid and basic substances) and tacky substances, and also solvents with the property of attacking plastics.

By means of the device according to the invention, it is also possible to safely store substances which are particularly sensitive to radiation. After the foil forming the container, external radiation now has to pass an additional barrier before it can impinge on the substance. Radiation here is to be understood as any form of naturally occurring or artificially generated radiation. This includes, on the one hand, electromagnetic radiation particularly in the range of 380 to 520 nm and, on the other hand, corpuscular radiation, in particular beta radiation.

The device according to the invention also permits unproblematic opening of the chamber by releasing the desired breaking point that is to be selectively opened. The substance which can be present in the chamber can then be transferred into the pouch for removal. At the same time, the device according to the invention acts as a dosing unit for dispensing and applying amounts of substance predetermined by the volume of the chamber.

The device according to the invention is accordingly characterized in that substances or components, which cause storage problems, of a mixture which is to be produced are made ready within one package, in particular a disposable package, for dispensing and mixing. In particular, for example, three components can be stored separately in the device: in the first portion of the device, two components which are needed to prepare an adhesive mixture, and, in the second portion, the third component in the form of a filling material which is adapted in terms of its chemical composition to the adhesive mixture.

Depending on the embodiment, the device is thus suitable not only for separate storage of several components, but also for mixing some of the components and for coordinated dispensing of the mixed components and of a further component which is adapted thereto and in terms of its rheological properties is usually different than the two other components.

It can also be advantageous if one of the foils, preferably the foil which is not thermoformed, has a peelable outer layer area and an inner layer area.

The presence of a peelable outer layer area in the first instance makes it easy to at least partially remove part of the foil. In this way, at least one chamber (or the chambers) containing one or more substances is visible.

The use of differently configured foils for the outer layer area, on the one hand, and for the foils forming the chamber, on the other hand, permits safe storage of the substances before the device is put to use.

In addition, the substances which are to be mixed are better protected in the storage state from external influences such as incident light or undesired pressure.

If one of the foils forming the chamber is transparent, it is possible, after removing the peelable outer layer area, to visually monitor the mixing procedure and/or the emptying of the chamber. In this way it is possible to achieve a more homogeneous mixing result and more complete emptying of the chamber into the pouch.

Depending on the substance to be applied, the inner layer of the foil coming into contact with the substance to be applied can be adapted to the properties of the substance. This allows the device to be used to store a large number of substances which differ in terms of their reactivity, without having to substantially modify the method for producing the device.

The invention thus allows, for example, dental material to be stored and dispensed safely and in a manner protected from contamination.

The first and second foils of the first portion can be multilayer foils. They have an optionally peelable outer layer area and an inner layer area.

The foils used are preferably those which have a sufficient diffusion density.

Depending on the nature of the substance to be stored, the foils should also be resistant to aggressive substances, for example, corrosive substances and/or substances which have solvent properties.

The foil components can be chosen from plastic foils, metal foils and ceramic foils.

Examples of suitable plastics are: PE, PP, PTFE, PET, PA, PBT, PVC, EVA, PVF (polyvinyl fluoride).

Examples of metal foils are: Al, Sn, Au, Ag, Fe.

Ceramic foils are to be understood as foils which have, for example, an SiOx-containing layer.

The foil can in principle have any desired structure and is adapted to the nature of the substances which are to be stored.

A foil structure has proven expedient which comprises in sequence, from outside to inside, PET, Al, PET, PE or PP, Al, PET, PE, if appropriate, also without the PET foil as middle foil.

Adhesive additives can also be present between the foils.

Examples of adhesive additives are: laminating adhesives or extrusion lamination media.

The optionally peelable outer layer area of the first foil is preferably opaque.

The inner layer area of the first foil is preferably transparent and, if appropriate, more flexible than the outer layer area.

The sequence, from outside to inside, of PET, Al or PP, Al has proven advantageous for the outer layer area.

The device comprises a first portion which has a first foil, for example, in the form of a cover foil, and a second foil, for example, in the form of a thermoformed foil, as is used in conventional blister packs.

Except for those areas forming the chamber or chambers, the foils of the first portion are preferably connected flat to one another, in particular securely sealed to one another, except for the passage area that is to be selectively opened.

The first foil can be connected to the second foil for example by heat-sealing, cold-sealing, adhesive bonding or ultrasonic welding with sonotrodes.

The device can also be produced in a simple way depending on the embodiment. The areas which can be peeled open can be produced in one operation, in particular by the action of the same energy application, even though these areas are situated on two different portions of the device.

A multilayer structure of the first foil and second foil can be obtained by laminating, calendering, coating of various single-foil layers, and if appropriate, also by vapor-deposition, for example, with metals.

To ensure that the substances introduced into the device and to be applied are protected from incident light, for example, the foils are preferably configured in such a way that, in an area surrounding the chamber, they are connected to one another by two spaced-apart sealing seams.

The second portion of the device usually likewise comprises two foils, usually a first foil in the form of a cover foil and a second foil in the form of a thermoformed foil. The first and second foils form a chamber for receiving a substance. The chamber can be opened in particular by means of the cover foil being pulled off. For this purpose, the first foil is preferably sealed onto the second foil in a peelable manner.

The device according to the invention thus comprises two portions with chambers, which are each formed by at least two foils, the foils of the individual portions being connected or sealed to one another in different ways, depending on the embodiment, so that the individual chambers can be opened in different ways.

The receptacle or receptacles present, if appropriate, in the chamber or chambers can be produced by the same methods as can be used to produce the device. The receptacle is in this case preferably produced by welding, adhesive bonding or sealing in the edge area of plastic-containing or metal-containing foils so that a cushion-shaped structure is obtained. The foils are connected in such a way that the receptacle can be opened under the action of external pressure, the aim being that the receptacle should preferably burst open in all directions under the effect of said pressure.

The device can in principle be of any desired shape, but the shape is preferably adapted to the nature of the substances stored.

The chamber or chambers are preferably round (circular or oval), but if appropriate also angular (square, rectangular or triangular).

The chambers have volumes which are adapted to their purpose, so that if used correctly, and with a plurality of components to be mixed together, they permit homogeneous mixing. The chamber adjacent to the pouch preferably has a volume which is suitable for receiving the total amount of substance which is to be mixed or has been mixed.

A chamber has, for example, a diameter of 5 to 20 mm, the dispensing instrument has a shaft diameter in the range of 2 to 4 mm. The substance volume to be applied is usually in the range of several tenths of a milliliter, preferably in the range of 0.03 to 0.5 ml. Depending on the embodiment, however, the substance volume to be applied can also be a few milliliters, in particular 5 to 10 ml.

The pouch is open to one side and can be designed in such a way that it can also receive a dispensing instrument in the storage state. With a suitably small diameter of the pouch opening toward the outside, the pouch can be in the form of a cannula, for example, or can itself serve as the application device.

The separation between the chamber or chambers and the pouch is designed, in terms of distance and in terms of the strength of the adhesion, in such a way as to form a desired breaking point.

The passage area is configured in such a way that, in the storage state, it forms a tight closure both with respect to the pouch and also, if appropriate, with respect to the second chamber.

Such a desired breaking point can be obtained, for example, by cold-sealing, heat-sealing, ultrasonic welding or adhesive bonding. In the case of heat-sealing, a different energy application, preferably a lower energy application, is provided compared to the other sealed areas. This can be controlled by temperature, pressure and/or holding time.

Another possibility is to arrange, between the first and the second foils in the area of the desired breaking point, foreign particles which reduce the adhesion, for example, peel foil punches or hot-melt adhesive spots. In this case, firmly sealing foils are preferably used as upper foil and lower foil.

The application instrument which is optionally present is preferably designed like a brush or a swab. An application instrument with a spherical tip bearing brush hairs or bristles has proven expedient. Pipets, cotton rods, sponges or spatulas can also be used as application instruments.

When using an application instrument, it is also expedient if the pouch is sealed off from the outside by the application instrument.

The device is preferably used for storing and dispensing substances, in particular small amounts thereof, such as, for example, those used in the dental field.

The device is particularly suitable for storing aggressive and/or photosensitive substances.

To use the device, the optionally present outer layer area is first pulled off at least partially until it is possible to see the chambers containing the substances to be mixed, which substances can also be present in separate receptacles.

Moreover, the two foils in the region of the passage area that can be selectively opened must be separated from one another so that a connection can be established between the chamber and the pouch.

It is likewise necessary to open the optional receptacle or receptacles containing a substance.

This is preferably done by exerting external pressure on the chamber, for example, between the user's thumb and index finger. In this way, the receptacle or receptacles containing the substance burst open. The internal pressure building up in the chamber finally leads to opening of the passage area that can be selectively opened.

If the device has a first chamber and a second chamber which can be connected to one another via a passage area that can be selectively opened, it is possible, by alternately pressing on the outer layer of the chambers containing the substances, to effect an alternating to and fro movement of the substances to be mixed through the selective opening created, before the mixed substances are transferred into the pouch adjacent to the chamber.

By kinking the device in the area between the chambers, the passage area or passage areas that can be selectively opened can be closed again. It is then virtually impossible for the mixed substances to flow back into the other chamber, so that the mixed substances can be transferred into the pouch by exerting pressure on the outer area of the foils forming the chamber.

If the inner layer area of the first foil is transparent, it is possible to visually monitor the mixing procedure and the emptying from chamber to chamber or into the pouch.

A dispensing instrument which is present in the pouch, or which is introduced into it only at this time or at a later time, is wetted and can then be used to apply the released substance.

It is also conceivable for the dispensing instrument to be moved in the direction toward the chamber in order to free the passage area that can be selectively opened and, if appropriate, to open the receptacle or receptacles located in the chamber. In this way too, the dispensing instrument is wetted.

If repeated application of the released substance is required, the dispensing instrument can be inserted back into the pouch.

The pouch or the dispensing instrument is preferably designed in such a way that, when the dispensing instrument is inserted back into the pouch, wetting of the outer area of the dispensing instrument does not take place.

This can be achieved, for example, by a channel-like configuration of the pouch and by adapting the configuration of the dispensing instrument to the pouch.

It is also conceivable to provide a dish-shaped or cup-shaped configuration of the pouch end of the thermoformed foil into which the substance is conveyed for repeated wetting of the application instrument without wetting the shaft of the application instrument.

The present invention thus also relates to a method for using the device, which method comprises the following steps:
a) provision of a device as has been described above,
b) application of pressure to the first chamber of the first portion, by which means the first substance is transferred into the pouch via the passage area that can be selectively opened and the application instrument which can be located in this pocket is wetted,
c) at least partial removal of the first substance from the pouch, usually with the application instrument located therein,
d) if appropriate, application of the first substance onto a surface, in particular onto hard dental tissue.
e) opening the second chamber of the second portion by pulling off a cover foil,
f) at least partial removal of the second substance from the second chamber, and
g) if appropriate, application of the second substance onto the site which was wetted with the first substance or came into contact with the first substance in step d).

Between step a) and step b), the second portion can be detached from the first portion of the device in order to facilitate the application of the substances which are located in the individual chambers.

The substances to be applied can be free-flowing, if appropriate, kneadable, or can also be present in powder form. The substances are preferably polymerizable.

Examples of polymerizable substances include photo-polymerizable or radical-polymerizable substances such as acrylic acid, methacrylic acid, maleic acid, both in monomer and polymer form or prepolymerized form, and derivatives thereof.

Free-flowing substances include all liquids and gels commonly used in the dental field, such as etching agents, primers and bonding agents and customary solvents.

The solvents can be chosen from among dipolar protic solvents and dipolar aprotic solvents. Examples which can be mentioned are: acetone, DMF, DMSO, alcohols, water.

All restorative and/or prosthetic substances common in the dental field, such as composites, compomers, ormocers, glass ionomer cements, silicate cements, phosphate cements, for example, as pastes or in powder form, can be stored in particular in the chamber of the second portion of the device and applied from there.

The substances are located preferably in the receptacle or receptacles, if appropriate, in the receptacle or receptacles and at the same time in the chamber containing the receptacle or receptacles.

The device according to the invention is described in more detail below with reference to the figures, in which.

BRIEF DESCRIPTION OF THE DRAWINGS

DETAILED DESCRIPTION OF THE DRAWINGS

The illustrative embodiments shown in the figures are given only as examples. The individual embodiments can be combined with one another at random.

Depending on the intended use, it can be advantageous if the second portion of the device is detached prior to activation of the first portion of the device.

However, independently of the number of chambers and/or receptacles in the chambers, it is also conceivable for the device always to have an at least partially peelable outer layer area.

Figure 1:
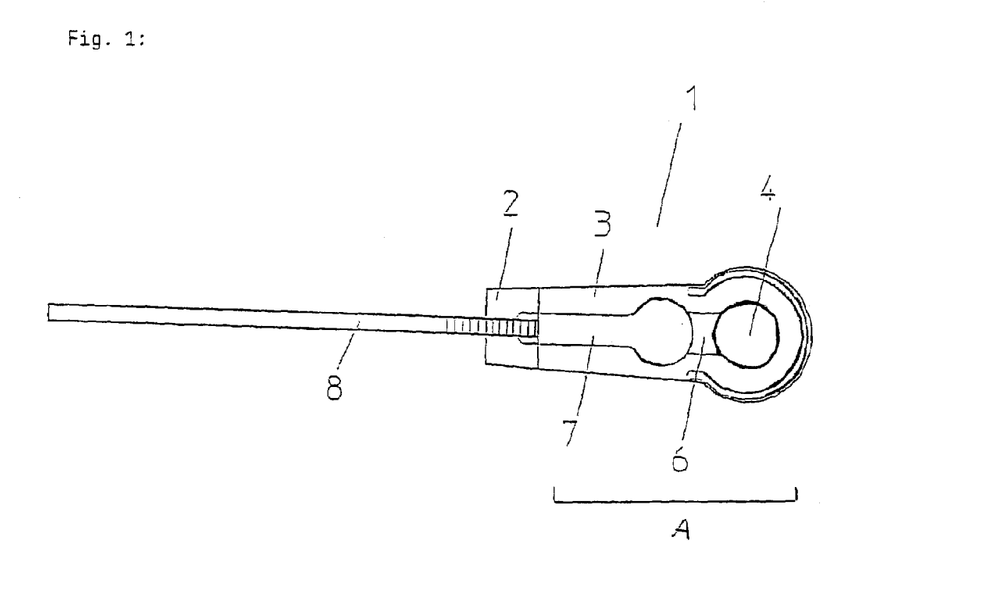
FIG. 1 shows a plan view of the device after the second portion has been detached.

FIG. 1 shows the device (1) according to the invention in a plan view, with a first portion (A) having a chamber (4) which is formed by a first foil (2) and a second foil (3), and with a passage area (6) that can be selectively opened, and with a pouch (7) in which a dispensing instrument (8) is located. The second portion (B) with the further chamber (11) cannot be seen here.

Figure 2:
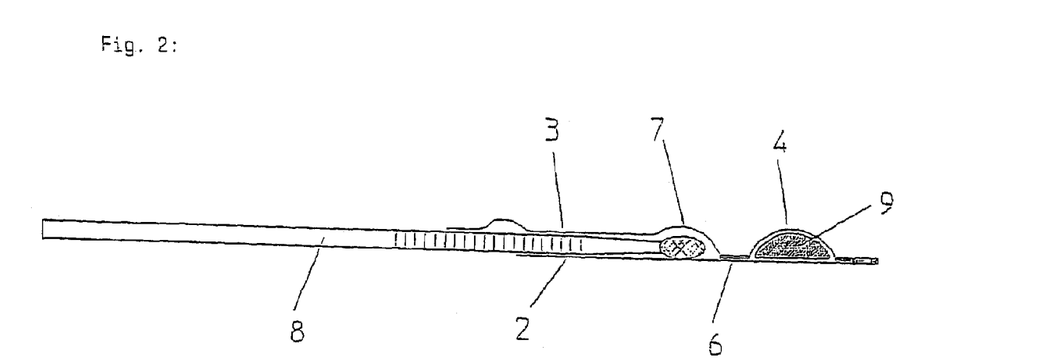
FIG. 2 shows a longitudinal section through the device with a chamber which comprises a receptacle, after the second portion has been detached.

FIG. 2 shows the device according to the invention in longitudinal section, with a receptacle (9) which is provided in the chamber of the first portion and which can contain a substance. The second portion (B) with the further chamber (11) cannot be seen here.

Figure 3:
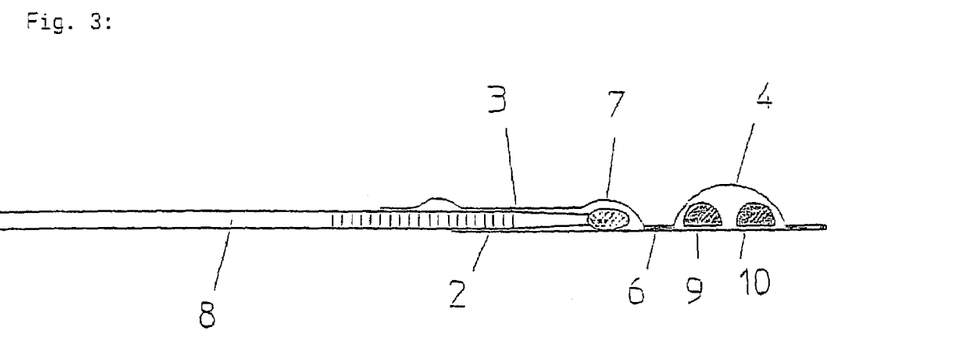
FIG. 3 shows a longitudinal section through the device with a chamber which comprises two receptacles, after the second portion has been detached.

In the device shown in longitudinal section in FIG. 3, the chamber (4) contains two receptacles (9, 10) which can contain substances. The second portion with the further chamber (11) cannot be seen here.

Figure 4:
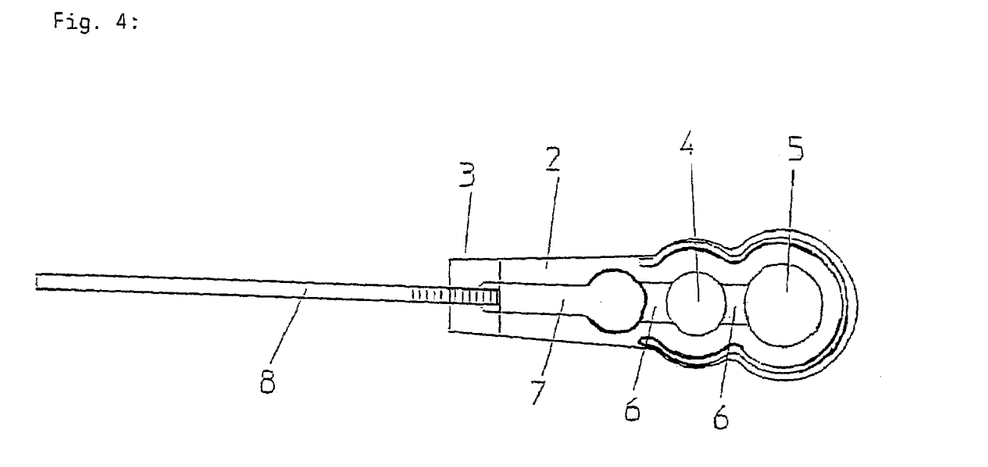
FIG. 4 shows a plan view of the device with two chambers, after the second portion has been detached.

FIG. 4 shows the device as in FIG. 1 with two chambers (4, 5) in a plan view, the chambers being connected to one another via a passage area (6) that can be selectively opened. The second portion (B) with the further chamber (11) cannot be seen here.

Figure 5:
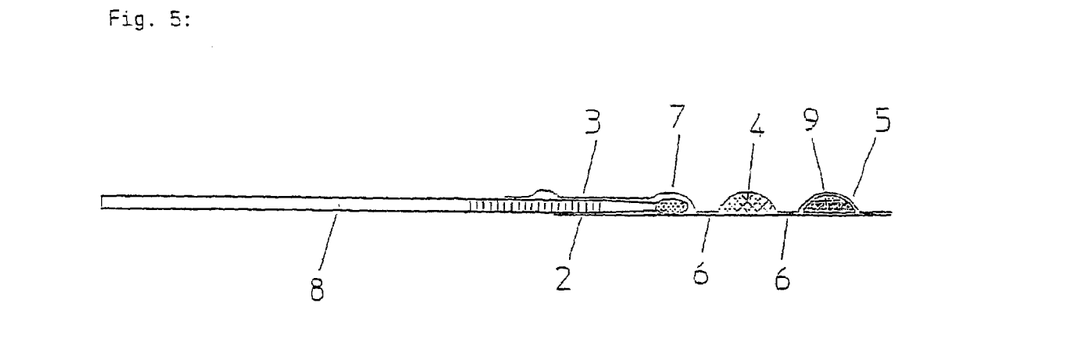
FIG. 5 shows a longitudinal section through the device with two chambers and one receptacle, after the second portion has been detached.

In the embodiment shown in FIG. 5, the device has two chambers (4, 5), said chambers being connected to one another via a passage area (6) that can be selectively opened, and the chamber (5) containing a receptacle (9). The second portion (B) with the further chamber (11) cannot be seen here.

Figure 6:
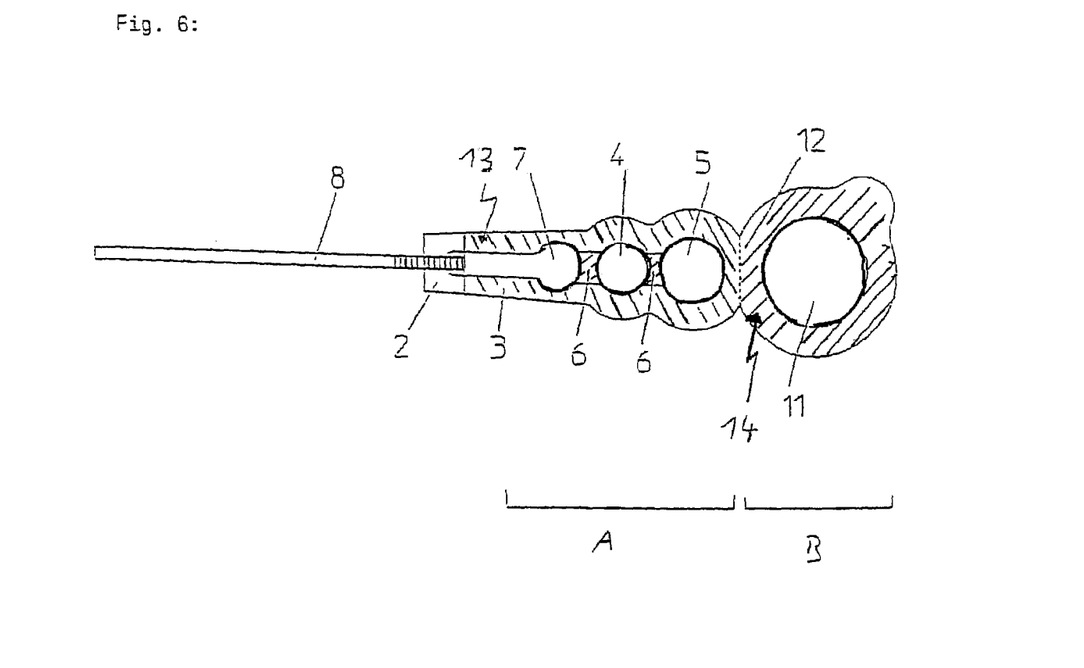
FIG. 6 shows a plan view of the device with three chambers which are arranged on two portions.

FIG. 6 shows an embodiment with two chambers (4, 5) on a first portion (A) which are connected to one another via a passage area (6) that can be selectively opened, and with a separate chamber (11) on a second portion (B). The separate chamber (11) is not connected to the other chambers via an area that can be selectively opened. In the embodiment shown, the separate chamber is designed so that it can be detached from the rest of the device via a perforation (12). The perforation (12) on the one hand permits, if appropriate, the complete detachment of the further chamber (11), while on the other hand it is intended to ensure that, when the further chamber (11) is opened by pulling off the cover foil, the entire outer foil is not pulled off. The foils forming the chambers are connected to one another in different ways in the areas (13, 14).

Whereas the foils in the first area (14) are sealed securely together (hatched lines from left to right), they are sealed to one another in such a way that they are peelable in the second area (13) (hatched lines from right to left).

Figure 7:
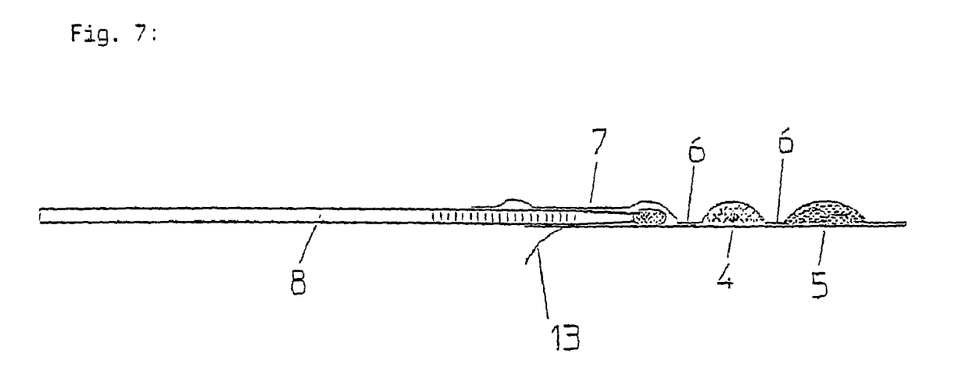
FIG. 7 shows a longitudinal section through the device with two chambers, where a foil has a peelable outer layer area, after the second portion has been detached.

In FIG. 7, an embodiment of the device is shown in longitudinal section with two chambers (4, 5), where one of the foils forming the device comprises a peelable outer layer area (14). The second portion with the further chamber (11) cannot be seen here.

The invention claimed is:

1. A device for storing and applying material, comprising:
a first portion having a first foil and a second foil;
a first chamber in said first portion;
a pouch in said first portion;
a dispensing instrument in said pouch, wherein a section of said dispensing instrument protrudes from said pouch;
a first selectively-openable passage area disposed between said first chamber and said pouch;
a second portion having a first chamber which is not identical to the first chamber of the first portion; and
a cover foil closing said first chamber of said second portion, wherein
said first chamber of said first portion receives a first substance,
said first chamber of said second portion receives a second substance,
said first portion and said second portion are non-identical,
a connection between said first portion and said second portion is not selectively-openable,
the first chamber of the second portion is not connected by a passage area to a chamber which is identical to the first chamber of the first portion,
the first chamber of the second portion does not communicate with a dispensing instrument; and
said first substance and said second substance have different rheological properties.

2. A device according to claim 1, wherein said first chamber of said second portion is openably sealed with a separately-peelable foil.

3. A device according to claim 2, wherein said separately-peelable foil is resealable.

4. A device according to claim 1, further comprising a second chamber in said first portion for receiving a third substance.

5. A device according to claim 4, wherein said first selectively-openable passage area is divided by said second chamber of said first portion into second and third selectively-openable passage areas, and said second selectively-openable passage area is disposed between said first chamber of said first portion and said second chamber of said first portion.

6. A device according to claim 5, wherein said third selectively-openable passage area is disposed between said second chamber of said first portion and said pouch.

7. A device according to claim 1, wherein said pouch is designed to receive a dispensing instrument.

8. A device according to claim 4, further comprising at least one receptacle in said first chamber of said first portion or said second chamber of said first portion.

9. A device according to claim 8, wherein said at least one receptacle, if located in said first chamber of said first portion, contains said first substance, and if located in said second chamber of said first portion, contains said third substance.

10. A device according to claim 8, further comprising said second substance in said second portion.

11. A device according to claim 9, wherein said substances are free flowing.

12. A device according to claim 10, wherein said second substance is pasty or kneadable.

13. A device according to claim 1, wherein one of said first foil and said second foil of said first portion comprises a peelable outer layer area and an inner layer area.

14. A device according to claim 13, wherein said peelable outer layer area is opaque and said inner layer area is transparent.

15. A method of using a device according to claim 1, comprising: storing or mixing or dispensing a free-flowing or pasty or kneadable substance in the device.

16. A dispensing device for dispensing dental materials, comprising:
a first chamber;
a second chamber separated from said first chamber by a selectively-openable passage for accommodating selective communication of said first and second chambers with one another;
an applicator adjacent to said first chamber and separated from said first chamber by a selectively-openable passage; and
a third chamber, non-identical to either said first and second chambers, adjacent to and continuously separated from said first chamber and said second chamber for accommodating a substance having different Theological properties from any substances in said first and second chambers,
wherein the third chamber is not connected by a passage area to either a chamber which is identical to said first chamber or said second chamber or to an applicator.

17. A dispensing device according to claim 16, wherein said substances are agents or components of agents for treating a tooth surface.

* * * * *

UNITED STATES PATENT AND TRADEMARK OFFICE
CERTIFICATE OF CORRECTION

PATENT NO. : 7,086,528 B2
APPLICATION NO. : 10/220611
DATED : August 8, 2006
INVENTOR(S) : Gioacchino Raia et al.

Page 1 of 1

It is certified that error appears in the above-identified patent and that said Letters Patent is hereby corrected as shown below:

Column 10,
Lines 57-58, delete "Theological" and insert in place thereof
--rheological--.

Signed and Sealed this

Twentieth Day of May, 2008

JON W. DUDAS
*Director of the United States Patent and Trademark Office*